(12) United States Patent
Schmidt

(10) Patent No.: US 12,697,072 B2
(45) Date of Patent: Aug. 4, 2026

(54) MULTIPARAMETERIC ESTIMATION OF CARDIORESPIRATORY FITNESS IN SEISMOCARDIOGRAPHY

(71) Applicant: AALBORG UNIVERSITET, Aalborg (DK)

(72) Inventor: Samuel Emil Schmidt, Aalborg (DK)

(73) Assignee: AALBORG UNIVERSITET, Aalborg (DK)

( * ) Notice: Subject to any disclaimer, the term of this patent is extended or adjusted under 35 U.S.C. 154(b) by 721 days.

(21) Appl. No.: 17/596,036

(22) PCT Filed: Jun. 5, 2020

(86) PCT No.: PCT/EP2020/065601
§ 371 (c)(1),
(2) Date: Dec. 2, 2021

(87) PCT Pub. No.: WO2020/245340
PCT Pub. Date: Dec. 10, 2020

(65) Prior Publication Data
US 2022/0296173 A1     Sep. 22, 2022

(30) Foreign Application Priority Data
Jun. 5, 2019     (EP) ..................................... 19178424

(51) Int. Cl.
*A61B 5/00*          (2006.01)
*A61B 5/02*          (2006.01)
(Continued)

(52) U.S. Cl.
CPC .............. *A61B 5/7267* (2013.01); *A61B 5/02* (2013.01); *A61B 5/02438* (2013.01);
(Continued)

(58) Field of Classification Search
CPC . A61B 5/7267; A61B 5/02438; A61B 5/1102; A61B 5/7225; A61B 2562/0219;
(Continued)

(56) References Cited

U.S. PATENT DOCUMENTS

| | | | |
|---|---|---|---|
| 11,504,047 B2* | 11/2022 | Khosrow-Khavar | ......................... G16H 50/50 |
| 2014/0221859 A1* | 8/2014 | Albert | .................... A61B 5/349 600/513 |
| 2019/0175072 A1 | 6/2019 | Schmidt et al. | |
| 2019/0336013 A1 | 11/2019 | Schmidt et al. | |
| 2020/0405170 A1* | 12/2020 | Khosrow-Khavar | .. A61B 5/318 |

FOREIGN PATENT DOCUMENTS

| | | |
|---|---|---|
| WO | 2013160538 A1 | 10/2013 |
| WO | 2016142575 A1 | 9/2016 |

(Continued)

OTHER PUBLICATIONS

Merriam-Webster, "Morphology", https://www.merriam-webster.com/dictionary/morphology (Year: 2025).*

(Continued)

*Primary Examiner* — Jonathan T Kuo
(74) *Attorney, Agent, or Firm* — Shore IP Group, PLLC; Eric J. Strianese

(57)          ABSTRACT
The proposed technology relates to the quantifying of cardiorespiratory fitness. It includes the obtaining (102) of a seismocardiogram (SCG) recorded with an accelerometer (14) configured to measure accelerations and vibrations of the chest wall of a person (18) caused by myocardial movement. Properties of a first signal feature (AC) in the seismocardiogram (SCG) are determined (104), wherein the first signal feature (AC) corresponds to the aortic valve closure (AC) of a heartbeat. A measure indicating cardiorespiratory fitness (VO2max) is then determined (106) based on the properties of first signal feature (AC).

14 Claims, 4 Drawing Sheets

(51) Int. Cl.

| | |
|---|---|
| *A61B 5/024* | (2006.01) |
| *A61B 5/11* | (2006.01) |
| *G16H 20/30* | (2018.01) |
| *G16H 40/63* | (2018.01) |
| *G16H 50/30* | (2018.01) |

(52) U.S. Cl.
CPC .......... *A61B 5/1102* (2013.01); *A61B 5/7225* (2013.01); *G16H 20/30* (2018.01); *G16H 40/63* (2018.01); *G16H 50/30* (2018.01); *A61B 2562/0219* (2013.01)

(58) Field of Classification Search
CPC . A61B 5/02007; A61B 5/7235; A61B 5/7264; A61B 5/02–5/0295; A61B 5/72–5/7296; G16H 20/30; G16H 40/63; G16H 50/30; G16H 50/00–50/80
See application file for complete search history.

(56) References Cited

FOREIGN PATENT DOCUMENTS

| | | | |
|---|---|---|---|
| WO | WO2017216375 | 12/2017 | |
| WO | WO-2017216375 A1 * | 12/2017 | ......... A61B 5/02028 |

OTHER PUBLICATIONS

International Search Report on corresponding PCT application (PCT/EP2020/0656001) from International Searching Authority (EPO) dated Sep. 3, 2020.
Written Opinion on corresponding PCT application (PCT/ EP2020/0656001) from International Searching Authority (EPO) dated Sep. 3, 2020.

* cited by examiner

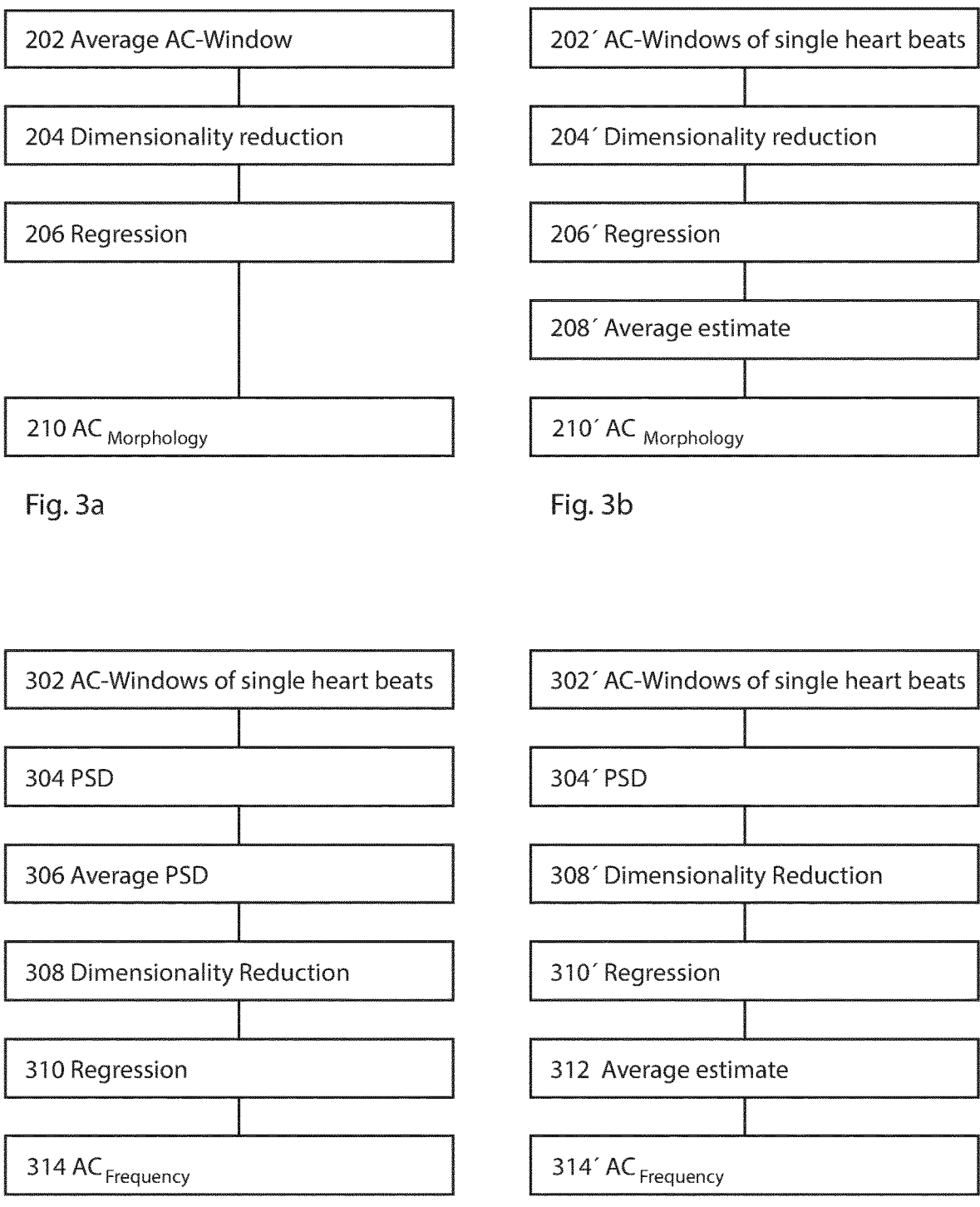

| 202 Average AC-Window |
| 204 Dimensionality reduction |
| 206 Regression |
| 210 AC Morphology |

Fig. 3a

| 202´ AC-Windows of single heart beats |
| 204´ Dimensionality reduction |
| 206´ Regression |
| 208´ Average estimate |
| 210´ AC Morphology |

Fig. 3b

| 302 AC-Windows of single heart beats |
| 304 PSD |
| 306 Average PSD |
| 308 Dimensionality Reduction |
| 310 Regression |
| 314 AC Frequency |

Fig. 4a

| 302´ AC-Windows of single heart beats |
| 304´ PSD |
| 308´ Dimensionality Reduction |
| 310´ Regression |
| 312 Average estimate |
| 314´ AC Frequency |

Fig. 4b

MULTIPARAMETERIC ESTIMATION OF CARDIORESPIRATORY FITNESS IN SEISMOCARDIOGRAPHY

CROSS-REFERENCE TO RELATED APPLICATION

This application is the National Phase, under 35 U.S.C. § 371(c), of International Application No. PCT/EP2020/065604, filed Jun. 5, 2020, which claims priority from European Application No. EP 19178424.8, filed Jun. 5, 2019. The disclosures of all of the referenced applications are incorporated herein by reference in their entirety.

FEDERALLY SPONSORED RESEARCH OR DEVELOPMENT

Not Applicable

TECHNICAL FIELD

The proposed technology relates generally to fitness applications, and particularly to methods and systems for determining an indication of cardiorespiratory fitness.

BACKGROUND

Cardiorespiratory fitness refers to the ability of the circulatory and respiratory systems to supply oxygen to muscles. The term is generally used for the ability to supply oxygen specifically to skeletal muscles during sustained physical activity, which may therefore be regarded as a subset of cardiovascular fitness.

Cardiorespiratory fitness is affected by physiological parameters, including heart rate, stroke volume, cardiac output, and maximal oxygen consumption. Regular exercise makes these systems more efficient by enlarging the heart muscle, enabling more blood to be pumped with each stroke, and increasing the number of small arteries in trained skeletal muscles.

A common measure of cardiorespiratory fitness is VO2 max corresponding to the maximum rate of oxygen consumption measured during an exercise that increases in intensity. Sometimes the measure is normalized by body weight.

There is both a clinical demand and a consumer demand for a low-cost and portable technology that can give an indication of cardiorespiratory fitness, or VO2 max.

Seismocardiography is the analysis of SeismoCardio-Grams (SCGs) showing sub-audible low-frequency vibrations at the chest wall caused by the beating heart. More generally, seismocardiography typically relates to non-invasive measurement of accelerations in the chest wall produced by myocardial movement. Heart sounds are audible components of the chest wall vibrations that typically are above 40-60 Hz, while SCG vibrations typically are below 25 Hz A seismocardiogram (SCG) is typically measured using an accelerometer. However, when an accelerometer is used, both low frequency seismocardiography components and audible components are simultaneously sampled. The signal from the accelerometer is then typically filtered such that it does not contain any audible components.

A SCG reveal different cardiovascular functions by which cardiorespiratory fitness can be determined. For example, seismocardiography is typically suitable for estimation of time intervals between features in the cardiac cycle.

The accelerometer signal is dominated by the high intensity of the low-frequency vibrations caused by the beating heart. If the accelerometer signal is low pass filtered, for example with an upper cutoff of 40 Hz, the influence of heart sounds is removed. In the filtered signal, or SCG signal, dominating features of the heart cycle are the Mitral valve Closure (MC), Isovolumic Movement (IM), Aortic valve Opening (AO), Isovolumic Contraction (IC), the Rapid Ejection (RE), Aortic valve Closure (AC), Mitral valve Opening (MO), and Rapid Filling (RF).

OBJECT

An object of the present invention is to meet the above-mentioned need for a technology that can give an indication of cardiorespiratory fitness, and in particular a technology having this capability and that is inexpensive and portable.

SUMMARY

According to a first aspect of the proposed technology, the aforementioned objects are accomplished by a method that comprises: obtaining a seismocardiogram (SCG) recorded with an accelerometer configured to measure accelerations and vibrations of the chest wall of a person caused by myocardial movement. The method further comprises: determining properties of a first signal feature (AC) in, or from, the seismocardiogram (SCG), wherein the first signal feature corresponds to, or relates to, the aortic valve closure (AC) of a heartbeat, or a cardiac cycle. The method may be for quantifying, or determining an indication of, cardiorespiratory fitness. The method may further comprise: determining a measure indicating, or determining an indication of, cardiorespiratory fitness (VO2 max) based on the properties of the first signal feature.

Here, obtaining a seismocardiogram does not specify the source from which the seismocardiogram is obtained, or how it is obtained. It is understood to encompass both a downloading, for example from a data storage or directly from an accelerometer, and an active use of an accelerometer. Alternatively to the specific step of obtaining the seismocardiogram, the first aspect of the proposed technology may be directed to a method for quantifying, or determining an indication of, cardiorespiratory fitness from a seismocardiogram (SCG) recorded with an accelerometer configured to measure accelerations and vibrations of the chest wall of a person caused by myocardial movement.

The proposed technology is centered on the realization that the signal feature in a seismocardiogram (SCG) corresponding to the aortic valve closure (AC) can be used for determining cardiorespiratory fitness. The seismocardiogram may cover a plurality of heartbeats, a single heartbeat, or a portion of a heartbeat, such as a diastolic segment of a heartbeat. It is understood that the first signal feature can correspond to the aortic valve closure (AC) of a single heartbeat, or of an average of heartbeats. A heartbeat is here understood to encompass a complete cardiac cycle. It is further understood that a signal feature may be a complex of joint features, for example a single peak connected to surrounding local minima.

Here, and throughout these specifications, determining, or quantifying, a measure indicating cardiorespiratory fitness is understood to not clearly and unambiguously indicate an abnormal cardiovascular or cardiorespiratory function, condition or structure, or a cardiovascular or cardiorespiratory disorder or disease. Determining a measure indicating cardiorespiratory fitness is however understood to include determining an indication of aerobic fitness, such as maximal oxygen consumption or uptake (VO2 max). Naturally, this measure may be influenced indirectly by some abnormal function of the heart, such as a disorder or a disease. However, the measure indicating cardiorespiratory fitness (VO2 max) does not point to a specific abnormal function and does not as such constitute a diagnostic measure.

The accelerometer may comprise a piezoelectric element. The signal may represent a voltage generated by the piezoelectric element. Thus, the signal strength or amplitude of a temporal feature may represent a voltage value for the temporal feature. It is understood that the output from the accelerometer does not include any audible components. For example, the recorded signal may have been filtered with a low-pass filter having an upper cut-off that is below 100 Hz, 60 Hz, 40 Hz, 20 Hz, 10 Hz, or 5 Hz.

In a second aspect of the proposed technology, a system is provided that comprises: an accelerometer configured to be placed on the chest of a person for measuring accelerations and vibrations of the chest wall of the person caused by myocardial movement. The system further comprises a processor operatively connected to the accelerometer, wherein the processor is configured to perform any of the steps of the method according to the first aspect of the proposed technology. The system may be for quantifying, or determining an indication of, cardiorespiratory fitness.

In a third aspect of the proposed technology, a system is provided that comprises: an accelerometer configured to be placed on the chest of a person for measuring accelerations and vibrations of the chest wall of the person caused by myocardial movement and obtaining a seismocardiogram (SCG). The system further comprises: a first determining module determining properties of a first signal feature in, or from, the seismocardiogram (SCG), wherein the first signal feature corresponds to, or relates to, the aortic valve closure (AC) of a heartbeat. The system may be for quantifying, or determining an indication of, cardiorespiratory fitness. The system may further comprise a second determining module determining a measure indicating, or determining an indication of, cardiorespiratory fitness (VO2 max) based on the properties of the first signal feature.

In a fourth aspect of the proposed technology, a computer program product is provided for being used in a system. The system may be for quantifying, or determining an indication of, cardiorespiratory fitness. The system comprises: an accelerometer configured to be placed on the chest of a person for measuring accelerations and vibrations of the chest wall of the person caused by myocardial movement, and a processor operatively connected to the accelerometer. The computer program product comprises program code instructions configured to, when executed by the processor of the system, cause the processor, or system, to: perform any of the steps of the method according to the first aspect of the proposed technology.

In a fifth aspect, a non-transient memory is provided on which a computer program product according to the fourth aspect of the proposed technology is stored.

Further optional details of the proposed technology are described below.

DETAILED DESCRIPTION

Determining the measure indicating cardiorespiratory fitness (VO2 max) may further be based on a first trained machine learning model. Determining the measure indicating cardiorespiratory fitness (VO2 max) may comprise, providing, or loading, a first machine learning model. The first machine learning model may be trained on properties of signal features operationally similar to the properties of the first signal feature (AC). The step may further comprise: determining the measure indicating cardiorespiratory fitness (VO2 max) by applying, or inputting, the properties of first signal feature (AC) to the first machine learning model. By the term "operationally similar" is understood that the properties of the signal features used in the training are defined or generated in the same manner, or has the same general properties, as the properties of first signal feature (AC).

In more general words, determining the measure indicating cardiorespiratory fitness (VO2 max) may comprise, or be composed of: providing a first machine learning model trained to determine the measure indicating cardiorespiratory fitness (VO2 max) based on the properties of first signal feature (AC), and applying, or inputting, the properties of first signal feature (AC) to the first machine learning model. In a more general wording, determining a measure indicating cardiorespiratory fitness (VO2 max) may comprise: determining a measure indicating cardiorespiratory fitness (VO2 max) by applying the properties of first signal feature (AC) to a trained first machine learning model.

Determining the properties of the first signal feature may comprise: determining a plurality of segments of the seismocardiogram (SCG), determining one or more noisy segments of the plurality of segments, and discarding the noisy segments. The non-discarded segments comprise the first signal feature, and the first signal feature is determined in the non-discarded segments. The segments may comprise diastolic and/or systolic segments. A diastolic segment is understood to be a segment of the seismocardiogram (SCG) that corresponds to the diastolic part of the cardiac cycle. Similarly, a systolic segment is understood to be a segment of the seismocardiogram (SCG) that corresponds to the systolic part of the cardiac cycle.

Determining the properties of the first signal feature may comprise: identifying one or more (first) fiducial points, or reference points, of the first signal feature. The measure indicating cardiorespiratory fitness may further be determined based on the one or more (first) fiducial points. The fiducial points may comprise: the local maxima (AC max) of the first signal feature, and/or the first local minima (AC min) immediately before to the local maxima (AC max). It is understood that the first local minima and the second local minima may correspond to a specific state in the cardiac cycle. For example, the second local minima may correspond to the Mitral valve Opening (MO).

A number of properties, or sub-features, of the first signal feature are described below. The properties are used in determining the measure indicating cardiorespiratory fitness. It has been found that each of the properties contributes to the quantifying, and it is understood that the properties can be used in isolation or in combination with each other. Preferably, all of the sub-features mentioned below are employed in the same method.

Thus, determining properties of the first signal feature may further comprise: determining an amplitude difference (ACPeakToPeak) between the local maxima (AC max) and the first local minima (AC min) immediately before to the local maxima (AC max) of the first signal feature. Determining the measure indicating cardiorespiratory fitness (VO2 max) may then further be based on the amplitude difference (ACPeakToPeak), or the amplitude difference (ACPeakToPeak) may constitute a property of first signal feature (AC), or form part of the properties of the first signal feature (AC).

Additionally or alternatively, determining properties of the first signal feature may further comprise: determining a first time separation (ACTimePeakToPeak) between the local maxima (AC max) of the first signal feature and the first local minima (AC min) immediately before to the local maxima (AC max) of the first signal feature. Determining the measure indicating cardiorespiratory fitness (VO2 max) may then further be based on the first time separation (ACTimePeakToPeak), or the first time separation (ACTimePeakToPeak) may constitute a property of first signal feature (AC), or form part of the properties of the first signal feature (AC).

Additionally, or alternatively, determining properties of the first signal feature may further comprise: determining a morphology measure (ACMorphology) of the first signal feature. Determining the measure indicating cardiorespiratory fitness (VO2 max) may then further be based on the morphology measure (ACMorphology), or the morphology measure (ACMorphology) may constitute a property of first signal feature (AC), or form part of the properties of the first signal feature (AC). It is understood that the morphology measure (ACMorphology) is determined in the time domain of the seismocardiogram (SCG). The morphology measure is understood to represent or indicate the shape, contour and/or outline of the first signal feature.

The determining of the morphology measure (ACMorphology) may comprise: determining a first window of the seismocardiogram (SCG), wherein the first window covers, or envelops, the first signal feature. Determining the morphology measure (ACMorphology) may then be based on the time domain of the first window.

It is understood that the first window may be determined from an average diastolic segment. Alternatively, the first window may be determined for each diastolic segment of the seismocardiogram (SCG). An average first window may then be determined before determining the morphology measure (ACMorphology).

In a preferred embodiment, individual morphology measures are determined for each first window, or for each diastolic segment, and the morphology measure (ACMorphology) is determined as an average of the individual morphology measures.

The width of the first window may be predetermined. Based on the time domain of the first window is understood to encompass the morphology measure (ACMorphology) being based on changes in signal value or amplitude over time in the first window. The first window may have a width in the range 200 ms to 500 ms, 250 ms to 450 ms, or 300 ms to 400 ms. This means that the technology can be applied at heart rates up to about 100 beats per minute. Determining the first window may comprise: identifying a fiducial point forming part of the first signal feature, and positioning the first window relative to the fiducial point. The fiducial point may be the local maxima (AC max) of the first signal feature. It is understood that the local maxima (AC max) of the first signal feature may be the local maxima (AC max) of a diastolic segment containing the first signal feature. The first window may start in the range 40 ms to 60 ms, or at 50 ms, before the fiducial point and end in the range 200 ms to 500 ms, 300 ms to 400 ms, or at 350 ms after the fiducial point.

Determining the morphology measure (ACMorphology) may comprise: providing, or loading, a second machine learning model. The second machine learning model may be trained on windows operationally similar to the first window of the seismocardiogram (SCG) (to determine morphology measures). It may further comprise: determining the morphology measure (ACMorphology) by applying, or inputting, the first window in the second machine learning model. The term "operationally similar" is understood to encompass each of the windows that the second model is trained on being defined or generated in the same manner, or comprising similar features, as the first window of the seismocardiogram (SCG).

In more general words, the determining of the morphology measure (ACMorphology) may comprise: providing a second machine learning model trained to determine the morphology measure (ACMorphology) based on the first window, and applying the first window, to the second machine learning model. More generally, the determining of the morphology measure (ACMorphology) may comprise: determining the morphology measure (ACMorphology) by applying the first window, to a trained second machine learning model. Here it is understood that the first window is represented in the time domain.

The second machine learning model may comprise: determining first dimensionality measures representing a dimensionality reduction of the first window, or the time domain thereof, and the second machine learning model may be trained to determine the morphology measure (ACMorphology) based on the first dimensionality measures. Then, the second machine learning model is trained on operationally similar dimensionality measures. The first dimensionality measures may be the principal components of a principal component analysis or the nodes acquired from an auto encoder constructed to compress the first window.

Determining properties of the first signal feature may further comprise: determining a frequency measure (ACFrequency) of the first signal feature. Determining the measure indicating cardiorespiratory fitness (VO2 max) may further be based on the frequency measure (ACFrequency), or the morphology measure (ACMorphology) may constitute a property of first signal feature (AC), or form part of the properties of the first signal feature (AC). The frequency measure (ACFrequency) may be determined in the frequency domain of the seismocardiogram (SCG).

Determining the frequency measure (ACFrequency) may comprise: determining a second window of the seismocardiogram (SCG), wherein the second window covers, or envelops, the first signal feature. Determining the frequency measure (ACFrequency) may then be based on the frequency domain of the second window.

Determining the frequency measure (ACFrequency) may further comprise: determining the power spectrum density, or spectral density, of the second window. Determining the frequency measure (ACFrequency) may then be based on the power spectrum density.

Similar to the first window, it is understood that the second window, or power spectrum density, may be determined for an average diastolic segment. Alternatively, the second window, or power spectrum density, may be determined for each diastolic segments, or second window, of the seismocardiogram (SCG). In a preferred embodiment, individual power spectrum densities are determined for each first window, or for each diastolic segment and an individual frequency measure is determined from each individual power spectrum density, and the frequency measure (ACFrequency) is determined as an average of the individual frequency measures.

The second window may have any of the features of the first window described above. The first window and the second window may be the same, or have the same features or properties. Above, based on the frequency domain of the second window is understood to encompass the frequency measure (ACFrequency) being based on changes in signal value or amplitude over frequency in the first window.

Determining the frequency measure (ACFrequency) may comprise: providing, or loading, a third machine learning model. The third machine learning model may be trained on the frequency domain, or power spectrum density, of windows operationally similar to the frequency domain, or power spectrum density, of the second window of the seismocardiogram (SCG) to determine frequency measures (ACFrequency). It may further comprise: determining the frequency measure (ACFrequency) by applying, or inputting, the second window, or the frequency domain or power spectrum density thereof, to the second machine learning model. By the term "operationally similar" is understood that the frequency domain, or power spectrum density, of each seismocardiogram (SCG) window used in the training is defined or generated in the same manner, or has the same general properties, as the frequency domain, or power spectrum density, of the second window.

In more general words, the determining of the frequency measure (ACFrequency) may comprise: providing a third machine learning model trained to determine the frequency measure (ACFrequency) based on the second window, or the frequency domain or the power spectrum density thereof, and applying the second window, or the frequency domain or the power spectrum density thereof, to the third machine learning model. More generally, the determining of the frequency measure (ACFrequency) may comprise: determining the frequency measure (ACFrequency) by applying the second window, or the frequency domain or the power spectrum density thereof, to a trained third machine learning model.

The third machine learning model may comprise: determining second dimensionality measures representing a dimensionality reduction of the second window, or the frequency domain or the power spectrum density thereof, and the third machine learning model may be trained to determine the frequency measure (ACFrequency) based on the second dimensionality measures. Then, the third machine learning model is trained on operationally similar dimensionality measures. The second dimensionality measured may be the principal components of a principal component analysis or the nodes acquired from an auto encoder constructed to compress the first window, or the power spectrum density.

Determining the measure indicating cardiorespiratory fitness (VO2 max) may be further based on the demographic data, such as gender, age, height, weight, and Body Mass Index (BMI). The first machine learning model may further be trained to determine the measure indicating cardiorespiratory fitness (VO2 max) based on the demographic data, and determining the measure indicating cardiorespiratory fitness (VO2 max) may be further comprise: applying the demographic data to the first machine learning model. In a more general wording, determining the measure indicating cardiorespiratory fitness (VO2 max) may comprise: applying the demographic data to the trained first machine learning model.

The method according to the first aspect of the proposed technology may further comprise: determining a heart rate variability (HRV). Determining the measure indicating cardiorespiratory fitness (VO2 max) may then further be based on the heart rate variability (HRV). The heart rate variability (HRV) may be determined from the seismocardiogram (SCG), or from an electrocardiogram (ECG) obtained simultaneously to, or in connection with, the seismocardiogram (SCG).

Determining the heart rate variability (HRV) may further comprise: determining a plurality of time intervals between fiducial points of the same type in succeeding heart beats, and determining the heart rate variability (HRV) as, or based on, the standard deviation of the plurality of time intervals.

Determining the measure indicating cardiorespiratory fitness (VO2 max) may comprise: providing, or loading, a first machine learning model trained on heart rate variability measures operationally similar to the heart rate variability (HRV). It may further comprise: determining the measure indicating cardiorespiratory fitness (VO2 max) by applying, or inputting, the heart rate variability (HRV) to the first machine learning model. By the term "operationally similar" is understood that the heart rate variability measures used in the training are defined or generated in the same manner, or has the same general properties, as the heart rate variability (HRV).

In a more general wording, the first machine learning model may further be trained to determine the measure indicating cardiorespiratory fitness (VO2 max) based on the heart rate variability (HRV), and determining the measure indicating cardiorespiratory fitness (VO2 max) may be further comprise: applying the heart rate variability (HRV) to the first machine learning model. More generally, determining the measure indicating cardiorespiratory fitness (VO2 max) may comprise: applying the heart rate variability (HRV) to the trained first machine learning model.

The method according to the first aspect of the proposed technology may further comprise: determining properties of a second signal feature in the seismocardiogram (SCG), wherein the second signal feature is different, or disjoint, from the first signal feature. Determining the measure indicating cardiorespiratory fitness (VO2 max) may then further be based on the properties of the second signal feature. It is understood that the second signal feature can be from a single heartbeat or constitute an average of several heartbeats, as described above for the first signal feature.

Determining the properties of the second signal feature may comprise: determining a plurality of systolic segments of the seismocardiogram (SCG), and discarding noisy systolic segments, wherein the non-discarded systolic segments comprises the second signal feature. A systolic segment is understood to be a segment of the seismocardiogram (SCG) that corresponds to the systolic part of the cardiac cycle.

The second signal feature may correspond to the mitral valve closure (MC) and/or aortic valve opening (AO) of a heart cycle. Determining the properties of the second signal feature may comprise: identifying one or more (second) fiducial points, or reference points, of the second signal feature. The measure indicating cardiorespiratory fitness may further be determined based on the one or more (second) fiducial points. The fiducial points may comprise: the zero crossing of the mitral valve closure (MC) and the first local maxima (AO max) of the aortic valve opening (AO) after the mitral valve closure (MC).

Determining properties of the second signal feature comprises may then comprise: determining a second time separation (SysTimeMCToAO) between the zero crossing of the mitral valve closure (MC) and the first local maxima (AO max) of the aortic valve opening (AO) after the mitral valve closure (MC). Determining the measure indicating cardiorespiratory fitness (VO2 max) may then further be based on the second time separation (SysTimeMCToAO).

In the proposed method, determining a measure indicating cardiorespiratory fitness (VO2 max) may further be based on a first trained machine learning model. Preferably, the method is based on at least three machine learning models, a first for determining the measure indicating cardiorespiratory fitness (VO2 max) as such, a second for determining the morphology measure (ACMorphology), and a third for determining the frequency measure (ACFrequency). This means that the first model may include the results of the second and third models. For example, the machine learning models may be based on linear regression, neural network regression, convolutional neural network regression or support vector machine regression.

BRIEF DESCRIPTION OF THE DRAWINGS

A more complete understanding of the abovementioned and other features and advantages of the present invention will be apparent from the following detailed description of the drawings, wherein:

FIGS. 4a-b are flow charts illustrating different embodiments for determining a frequency measure.

DESCRIPTION OF THE DRAWINGS

Figure 1:
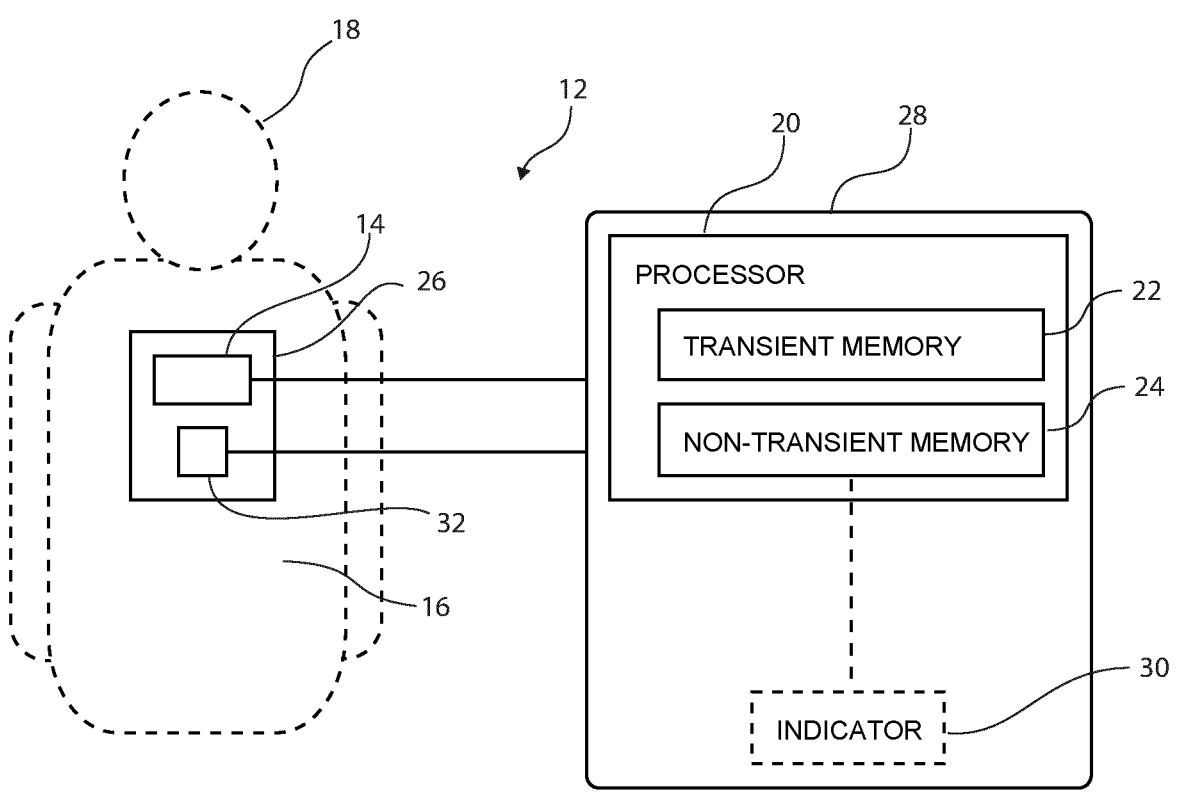
FIG. 1 is a schematic illustration of an embodiment of a system for determining an indication of cardiorespiratory fitness.

FIG. 1 schematically illustrates an embodiment of a system for quantifying cardiorespiratory fitness. The system 12 has an accelerometer 14 in the form of a piezoelectric element that can be placed on the chest of a person 18 and for measuring vibrations of the chest wall caused by movements of the heart. A processor 20 is connected to the accelerometer 14. The processor 20 has a transient memory 22 which can store a signal received from the accelerometer 14, and by which it can execute program code instructions. The system 12 comprises a support 26 that supports the accelerometer 14 and a housing 28 that accommodates the processor 20. The system 12 also has a non-transient memory storing program code instructions for the processor 20. For example, the system 12 as a whole can be an integral part of a smart-phone, or all parts except the accelerometer 20 and the support 26 can form part of a smart-phone. In one embodiment, the accelerometer 14 is an integrated accelerometer of a smart-phone.

In one embodiment of the system 12, it additionally has an indicator 30 operatively connected with the processor 20. The indicator 30 can, for example, have an LCD display, or the like, that can display output information from the processor 20, such as a number indicating a measure of cardiorespiratory fitness.

The system also comprises electrocardiogram electrodes 32 (two leads plus ground) supported by the support 26. The electrodes 32 are connected to the processor 20.

The primary function of the accelerometer 14 is to sample a seismocardiogram (SCG) for further analysis. The primary function of the electrodes 32 is to sample an electrocardiogram (ECG) that is used for segmentation of the seismocardiogram (SCG).

Figure 2:
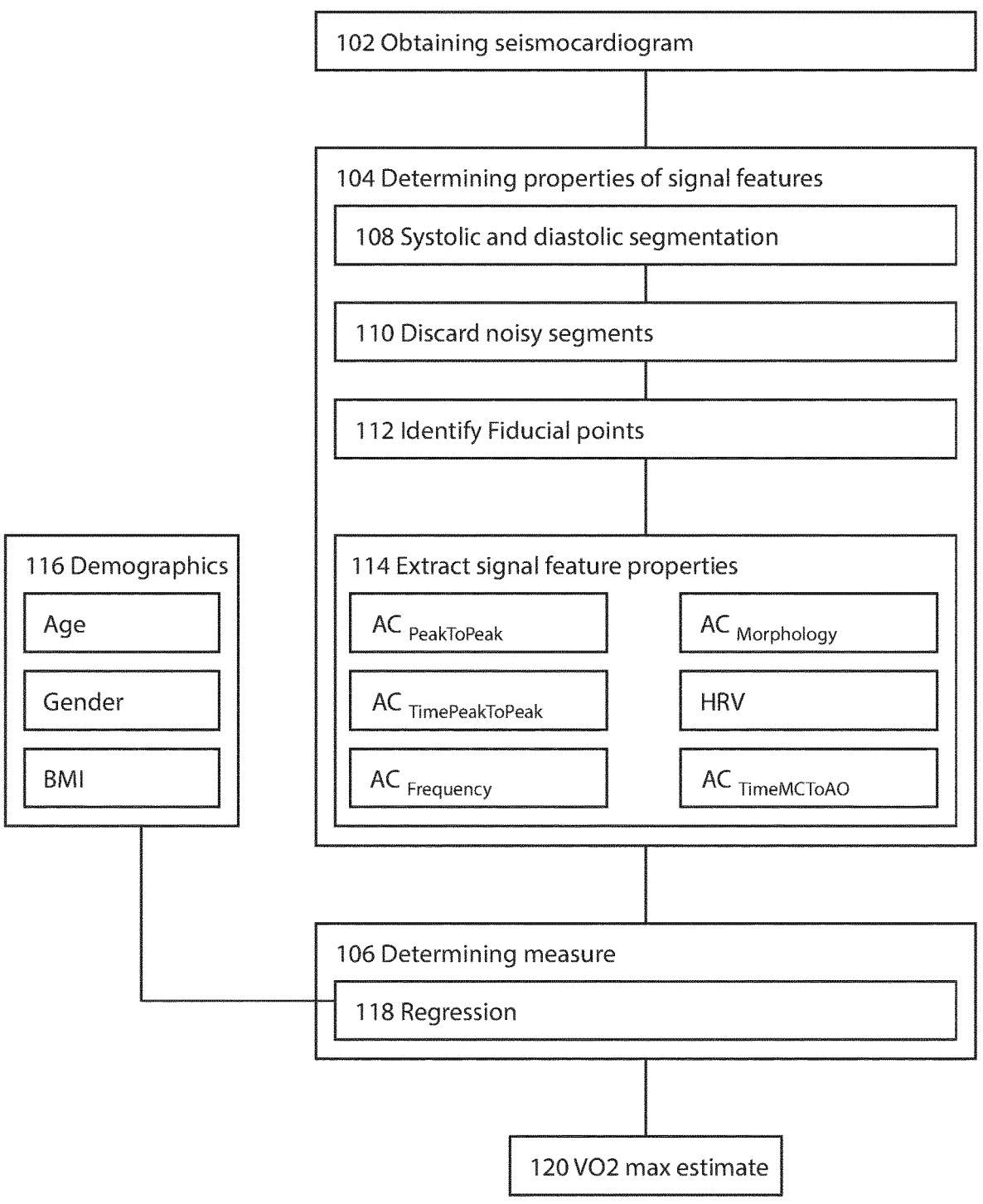
FIG. 2 is a flow chart illustrating the basic steps of a method employed in the system described in relation to FIG. 1, FIGS. 3a-b are flow charts illustrating different embodiments for determining a morphology measure.

The program code instructions in the non-transient memory 24 cause the processor 20 to perform a method that is shown in FIG. 2. A seismocardiogram (SCG) is obtained 102 with the accelerometer 14 placed on the chest of a person 18. In an alternative embodiment, the SCG is downloaded from a server to which it previously has been uploaded. Properties of two signal features are determined 104 in the seismocardiogram (SCG). How this is achieved is described in detail below. A measure indicating cardiorespiratory fitness (VO2 max) is then determined 106 based on the properties of first signal feature.

A plurality of systolic and diastolic segments is determined 108 in the SCG. This is achieved by an automated segmentation method using an electrocardiogram (ECG) simultaneously acquired by the electrodes 32 as reference. In alternative embodiments, the segmentation is based on the SCG as such, e.g. similar to the technology described in U.S. Pat. No. 8,235,912 (B2). Noisy segments are then discarded 110, for example as described in WO2017216375 (A1).

Figure 5:
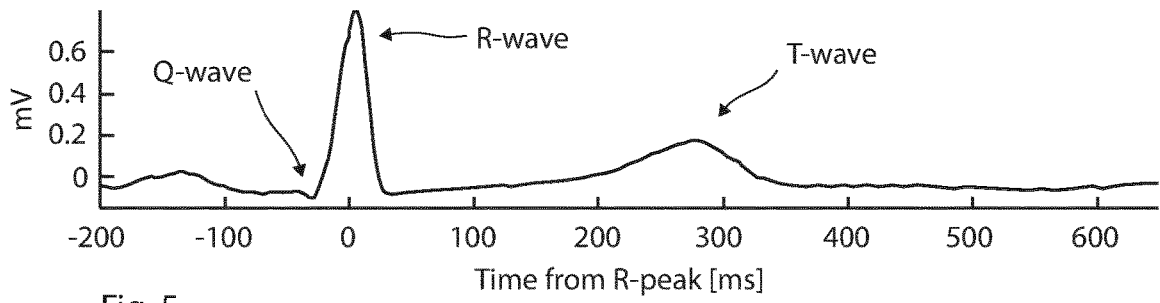
FIG. 5 is a graph showing an electrocardiogram of a heart cycle.
Figure 6:
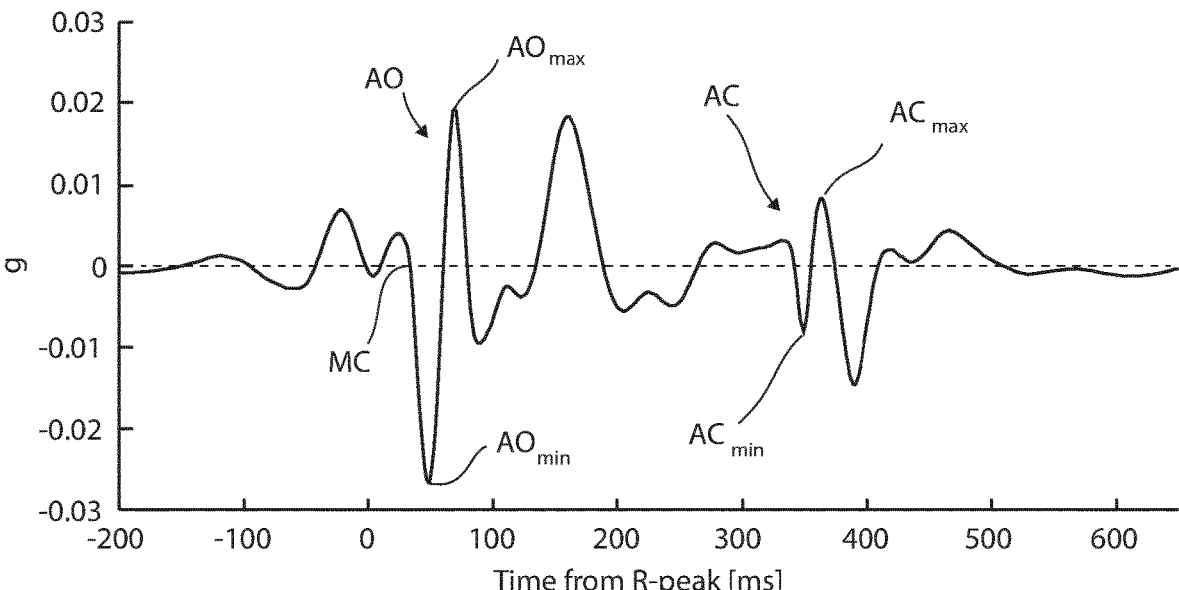
FIG. 6 is graph showing a seismocardiogram of a heart cycle recorded simultaneously to the electrocardiogram of FIG. 5.

FIG. 5 shows an electrocardiogram (ECG) with the signal from the electrodes 32 in the unit Volt (mV) as function of time (ms). The time has been reset with respect to the peak of the R-wave. FIG. 6 shows a simultaneously recorded seismocardiogram (SCG) with the accelerometer signal in the unit of gravitational force equivalents (g) as a function of time (ms) reset in the same manner as the electrocardiogram (ECG).

Each of the resulting diastolic segments includes or comprises a first signal feature corresponding to the aortic valve closure (AC) of a single heartbeat. Similarly, each of the resulting systolic segments includes a second signal feature corresponding to the combined mitral valve closure (MC) and the aortic valve opening (AO) of a heart cycle.

Fiducial points are then identified 112 for respective signal feature in the systolic and diastolic segments, similar to identifications described in WO2017216375 (A1). The following fiducial points are determined in each diastolic segment, or for each first signal feature:

> the local maxima ($AC_{max}$) of the aortic valve closure (AC), and
>
> the first local minima ($AC_{min}$) immediately before to the local maxima ($AC_{max}$).

The following fiducial points are determined in each systolic segment, or for each second signal feature:

> the zero crossing of the mitral valve closure (MC), and
>
> the first local maxima (AO max) of the aortic valve opening (AO) after the mitral valve closure (MC).

The abovementioned fiducial points are indicated in FIG. 6. Properties of the signal features are then determined 114 based at least in part on the fiducial points.

A first property of the first signal feature corresponding to the aortic valve closure (AC) is the amplitude difference (ACPeakToPeak) between the local maxima (AC max) and the first local minima (AC min). A measure (ACPeakToPeak) representing the property is determined from the mean of the diastolic segments. A second property of the same signal feature is the (first) time separation (ACTimePeakToPeak) between the local maxima (AC max) and the first local minima (AC min) immediately before to the local maxima (AC max). A measure (ACTimePeakToPeak) representing the property is determined from the mean of the diastolic segments normalized to a standard deviation of one. A third property is the morphology of the of the first signal feature represented by a morphology measure $(AC_{Morphology})$. A fourth property is a frequency measure $(AC_{Frequency})$ of the of the first signal feature. The determining of the latter two properties is further described below.

Figure 7:
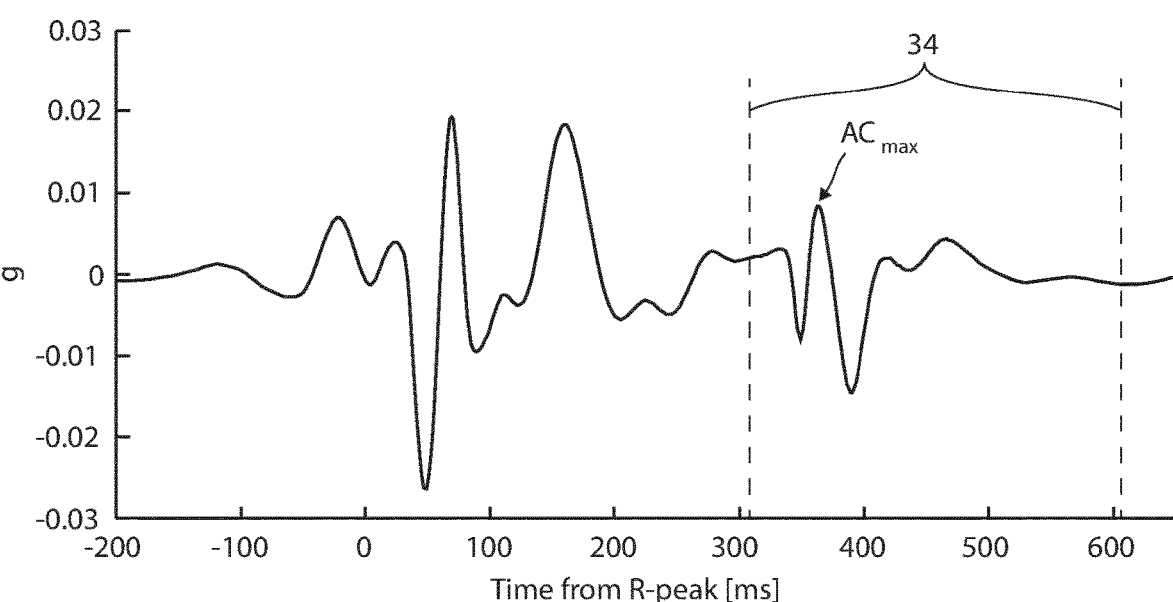
FIG. 7 is graph showing a window overlaid on the seismocardiogram of FIG. 6.

When determining the morphology measure $(AC_{Morphology})$, a (first) window 34 is identified in the seismocardiogram (SCG). The window 34 starts 50 ms before the local maxima (AC max) and ends 250 ms after the local maxima (AC max). A corresponding window 34 is indicated in FIG. 7 showing the seismocardiogram (SCG) of FIG. 6.

The morphology measure $(AC_{Morphology})$ is determined using an early averaging. The steps relating to the early averaging are illustrated in FIG. 3a. An average diastolic segment is determined and the window 34 is then identified 202 in the average diastolic segment. The amplitudes in the window 34 are normalized to a standard deviation of one to reduce the influence of amplitude variations. A dimensionality reduction 204 is then performed using principal component analysis (PCA) conducted on the window 34 of the average diastolic segment for identifying principal components. In an alternative embodiment, the dimensionality reduction 204 is performed using an auto encoder (AE) with the window 34 of the diastolic segment as input and constructed such that the auto encoder (AE) compresses the window into a few nodes in a neural network, for example 10 nodes. A regression 206 is then performed using a linear regression function with the principal components, or nodes, as input. In alternative embodiments, the regression function is based on neural network regression, convolutional neural network regression, or Support vector machine regression. The regression 206 results in a morphology measure $(AC_{Morphology})$ 210 representing or quantifying the shape of the first signal feature, or the complex of the seismocardiogram (SCG) relating to the aortic valve closure (AC).

In an alternative embodiment, the morphology measure $(AC_{Morphology})$ is determined using a late averaging. The steps relating to the late averaging are illustrated in FIG. 3b. The window 34 is identified 202' in each diastolic segment. The amplitudes in each window 34 are normalized to a standard deviation of one to reduce the influence of amplitude variations. A dimensionality reduction 204' is then performed using principal component analysis (PCA) conducted on a matrix of the windows 34 for identifying principal components. In an alternative embodiment, the dimensionality reduction 204' is performed using an auto encoder (AE) with a matrix of the windows 34 as input compressing them into a number of nodes, such as ten, in a neural network. A regression 206 is then performed using a linear regression function with the principal components, or nodes, as input. In alternative embodiments, the regression function is based on neural network regression, convolutional neural network regression, or support vector machine regression. The regression 206' results in an individual measure for each window of a diastolic segment. An average over the individual measures is calculated 208' yielding the morphology measure $(AC_{Morphology})$ 210'.

When determining the frequency measure $(AC_{Frequency})$, the same windows 34 in the diastolic segments are used as when determining the morphology measure $(AC_{Morphology})$.

The frequency measure $(AC_{Frequency})$ is determined using an early averaging. The steps relating to the early averaging are illustrated in FIG. 4a. The window 34 is identified 302' in each average diastolic segment. The amplitudes in the windows 34 are normalized to a standard deviation of one to reduce the influence of amplitude variations. The power spectrum density (PSD) is then determined 304 in each window 34. An average power spectrum density (PSD) is determined 306, which is used in a dimensionality reduction 308 similar to the dimensionality reductions 204 described above in relation to the early averaging approach for determining the morphology measure $(AC_{Morphology})$. A regression 310 is then performed using the resulting principal components, or nodes, as input, similar to the regressions 206 described in relation to the abovementioned early averaging approach. The regression 310 results in a frequency measure $(AC_{Frequency})$ 314 representing or quantifying the properties in the frequency domain of the average window, and in extension of the first signal feature.

In an alternative embodiment, the frequency measure $(AC_{Frequency})$ is determined using a late averaging. The steps relating to the late averaging are illustrated in FIG. 4b. The window 34 is identified 302' in each diastolic segment. The amplitudes in each window 34 are normalized to a standard deviation of one to reduce the influence of amplitude variations. The power spectrum density (PSD) is determined 304 in each window 34. Instead of calculating an average power spectrum density (PSD), a dimensionality reduction 308' similar to the dimensionality reductions 204' described above in relation to the late averaging approach for determining the morphology measure $(AC_{Morphology})$ is performed on a matrix of the determined power spectrum densities. A regression 310' is then performed using the principal components, or nodes, for each window as input, similar to the regressions 206' described in relation to the abovementioned late averaging approach. The regression 310' results in a number of individual measures, each corresponding to a window of a diastolic segment. A frequency measure $(AC_{Frequency})$ 314' is then determined as the mean 312, or in an alternative embodiment the median, of the individual measures.

The abovementioned four properties of the first signal feature are used in the input for determining 106 the measure indicating cardiorespiratory fitness (VO2 max). Additionally, the heart rate variability (HRV) and a property of the second signal feature corresponding to the mitral valve closure (MC) and the aortic valve opening (AO) of a heart cycle are used as input.

The heart rate variability (HRV) is determined by first identifying succeeding heart beats in the seismocardiogram (SCG), and then calculating as the length of a the time interval between the same fiducial points, such as the local maxima $(AC_{max})$ of the aortic valve closure (AC), in succeeding heart beats.

The property of the second signal feature is the time separation (SysTimeMCToAO) between the zero crossing of the mitral valve closure (MC) and the first local maxima (AO max) of the aortic valve opening (AO) after the mitral valve closure (MC). A measure representing the property is determined from the mean of the diastolic segments normalized to a standard deviation of one.

Demographic measures are also provided 116 representing the age, gender, and body-mass index of the person.

All the above-mentioned measures are used as input in a multi-parametric regression 118 for determining 106 the measure indicating cardiorespiratory fitness (VO2 max) 120. Effectively, in the preferred embodiment the regression is represented by:

$$VO2maxPrKG = \omega 1 \; ACPeakToPeak + \omega 2 \; ACTimePeakToPeak +$$
$$\omega 3 \; ACFrequency + \omega 4 \; ACMorphology + \omega 5 \; HRV +$$
$$\omega 6 \; SysTimeMCToAO + \omega 7 \; Age + \omega 8 \; Gender + \omega 9 \; BMI$$

In alternative embodiments, fewer measures are used in the regression 118. Here, the measure indicating cardiorespiratory fitness (VO2 max PrKG) is normalized with respect to bodyweight.

Proof-of-Concept

The proposed technology has been validated in 145 measurements from 133 subjects. In each measurement, a seismocardiogram was recorded and immediately afterwards the subject underwent traditional VO2 max test. The latter was considered the golden standard and a performance measure was determined as the correlation between the VO2 max predicted by the proposed technology and the golden standard VO2 max. In the final validation the standard error of estimate (SEE) was used to evaluate the error between the predicted and golden standard VO2 max.

The Validation of the individual features was conducted using a 5-fold cross validation, where 3-folds were used for training, one fold for validation and one fold for test. The validation of the final score was conducted using 5 times repetition of 10 fold-cross validation.

For the frequency measure (ACFrequency), the best performing feature extraction method was the linear regression after PCA using early averaging, see table 1. For the morphology measure (ACMorphology), the best performing feature extraction method was the linear regression after PCA using late averaging, see table 2.

The correlations between the reference, or golden standard, VO2 max and the predicted VO2 max, or determined measure indicating cardiorespiratory fitness (VO2 max), are shown in table 3. Results including and excluding the frequency measure (ACFrequency) and the morphology measure (ACMorphology) are shown. It can be concluded from table 3 that both these measures increase the correlation of the reference VO2 max and the predicted VO2 max. It can be concluded that the addition of both the frequency measure (ACFrequency) and the morphology feature (ACMorphology) improved performance of the proposed method for determining a measure (VO2 max) indicating cardiorespiratory fitness, or VO2 max.

TABLE 1

Correlation between the frequency measure ($AC_{Frequency}$) and the measure indicating cardiorespiratory fitness (VO2max) depending on the use of Dimensionality Reduction and regression method

| | Dimensionality Reduction | | | | | |
| --- | --- | --- | --- | --- | --- | --- |
| | None | | AE | | PCA | |
| Regression method | Linear Regression | Neural Network | Linear Regression | Neural Network | Linear Regression | Neural Network |
| Early avg. | 0.737 | 0.577 | 0.698 | 0.683 | 0.740 | 0.681 |
| Late avg. | 0.736 | 0.682 | 0.699 | 0.734 | 0.709 | 0.656 |

TABLE 2

Correlation between the morphology measure ($AC_{Morphology}$) and the measure indicating cardiorespiratory fitness (VO2max) depending on the use of Dimensionality Reduction and regression method

| | Dimensionality Reduction | | | | | |
| --- | --- | --- | --- | --- | --- | --- |
| | None | | AE | | PCA | |
| Regression method | Linear Regression | Neural Network | Linear Regression | Regression method | Linear Regression | Neural Network |
| Early avg. | 0.651 | 0.446 | 0.679 | 0.714 | 0.717 | 0.508 |
| Late avg. | 0.715 | 0.663 | 0.657 | 0.738 | 0.744 | 0.659 |

TABLE 3

Correlation between the frequency measure ($AC_{Frequency}$), the the morphology measure ($AC_{Morphology}$), and reference VO2max depending on the use of dimensionality reduction and regression method.

| Properties/measures | Age Gender Weight $AC_{TimePeakToPeak}$ $AC_{PeakToPeak}$ $Sys_{TimeMCToAO}$ | Age Gender Weight $AC_{TimePeakToPeak}$ $AC_{PeakToPeak}$ $Sys_{TimeMCToAO}$ $AC_{Frequency}$ | Age Gender Weight $AC_{TimePeakToPeak}$ $AC_{PeakToPeak}$ $Sys_{TimeMCToAO}$ $AC_{Morphology}$ | Age Gender Weight $AC_{TimePeakToPeak}$ $AC_{PeakToPeak}$ $Sys_{TimeMCToAO}$ $AC_{Morphology}$ $AC_{Frequency}$ |
| --- | --- | --- | --- | --- |
| 10-fold cross validation | | | | |
| Correlation to VO2max | 0.8130 | 0.8227 | 0.8340 | 0.8365 |
| SEE ((mL/min)/kg) | 5.9283 | 5.7879 | 5.6128 | 5.5755 |

TABLE 3-continued

Correlation between the frequency measure ($AC_{Frequency}$), the the morphology measure ($AC_{Morphology}$), and reference VO2max depending on the use of dimensionality reduction and regression method.

| Properties/measures | Age Gender Weight $AC_{TimePeakToPeak}$ $AC_{PeakToPeak}$ $Sys_{TimeMCToAO}$ | Age Gender Weight $AC_{TimePeakToPeak}$ $AC_{PeakToPeak}$ $Sys_{TimeMCToAO}$ $AC_{Frequency}$ | Age Gender Weight $AC_{TimePeakToPeak}$ $AC_{PeakToPeak}$ $Sys_{TimeMCToAO}$ $AC_{Morphology}$ | Age Gender Weight $AC_{TimePeakToPeak}$ $AC_{PeakToPeak}$ $Sys_{TimeMCToAO}$ $AC_{Morphology}$ $AC_{Frequency}$ |
|---|---|---|---|---|
| Full dataset | | | | |
| Correlation to VO2max | 0.8276 | 0.8617 | 0.8594 | 0.8678 |
| SEE ((mL/min)/kg) | 5.7059 | 5.1865 | 5.2002 | 5.0510 |

The invention claimed is:

1. A method for quantifying cardiorespiratory fitness of a person, the method comprising:

(a) obtaining a seismocardiogram (SCG) recorded with an accelerometer placed on the chest of the person and configured to measure accelerations and vibrations of the chest wall of the person caused by myocardial movement;

(b) determining properties of a first signal feature in the SCG, wherein the first signal feature corresponds to an aortic valve closure of a heartbeat, wherein determining properties of the first signal feature comprises:

(b)(i) determining a frequency measure of the first signal feature; and (b)(ii) determining a morphology measure of the first signal feature by (1) determining a first signal window of the SCG that covers the first signal feature, (2) providing a first machine learning model trained to determine the morphology measure based on a time-domain waveform representation of the corresponding first signal window, and (3) inputting the time-domain waveform representation of the first signal window to the first machine learning model, wherein (4) the morphology measure indicates the shape, contour and/or outline of the first signal feature, wherein the frequency measure and the morphology measure are properties of the first signal feature; and (c) determining a measure indicating the cardiorespiratory fitness of the person by (5) providing a second machine learning model trained to determine the measure indicating cardiorespiratory fitness based at least on corresponding properties of the first signal feature, and (6) inputting at least the properties of the first signal feature to the second machine learning model.

2. The method according to claim 1, wherein determining the properties of the first signal feature further comprises:

(b)(iii) determining a plurality of diastolic segments of the SCG; and (b)(iv) discarding noisy diastolic segments, wherein the non-discarded noisy diastolic segments comprise the first signal feature.

3. The method according to claim 2, wherein determining the properties of the first signal feature further comprises:

(b)(v) identifying one or more fiducial points of the first signal feature;

wherein the measure indicating cardiorespiratory fitness is further determined based on the one or more fiducial points;

wherein the fiducial points comprise at least one of a local maximum of the first signal feature, and a first local minimum immediately before the local maximum.

4. The method according to claim 1, wherein determining properties of the first signal feature further comprises:

(b)(iii) determining an amplitude difference between a local maximum of the first signal feature and a first local minimum immediately before the local maximum of the first signal feature;

wherein determining the measure indicating cardiorespiratory fitness is further based on the amplitude difference.

5. The method according to claim 1, wherein determining properties of the first signal feature further comprises:

(b)(iii) determining a first time separation between a local maximum of the first signal feature and a first local minimum immediately before the local maximum of the first signal feature; and wherein determining the measure indicating cardiorespiratory fitness is based on the first time separation.

6. The method according to claim 1, wherein determining the morphology measure comprises:

determining an SCG window having a time domain, wherein the SCG covers the first signal feature;

wherein determining the morphology measure is based on the time domain of the SCG window.

7. The method according to claim 6, wherein the SCG window has a width in the range 200 ms to 500 ms.

8. The method according to claim 6, wherein determining the frequency measure comprises:

determining an SCG window having a frequency domain, wherein the SCG window covers the first signal feature; and determining the frequency measure based on the frequency domain of the SCG window.

9. The method according to claim 1, further comprising:

(d) determining a heart rate variability;

wherein determining the measure indicating cardiorespiratory fitness is further based on the heart rate variability.

10. The method according to claim 1, further comprising:

(d) determining properties of a second signal feature in the SCG, wherein the second signal feature is different from the first signal feature;

wherein determining the measure indicating cardiorespiratory fitness is further based on the properties of the second signal feature; and wherein the second signal feature corresponds to at least one of a mitral valve closure and an aortic valve opening of a heart cycle.

11. The method according to claim 10, wherein determining properties of the second signal feature further comprises:

determining a second time separation between a zero crossing of the mitral valve closure and a first local maximum of the aortic valve opening after the mitral valve closure; and wherein determining the measure indicating cardiorespiratory fitness is further based on the second time separation.

12. The method according to claim 1, wherein determining the first signal window of the SCG that covers the first signal feature comprises identifying a fiducial point of the first signal feature and positioning the first signal window relative to the fiducial point.

13. A system for quantifying or determining an indication of cardiorespiratory fitness of a person, the system comprising:

an accelerometer configured to be placed on the chest of the person for measuring accelerations and vibrations of the chest wall of the person caused by myocardial movement; and a processor operatively connected to the accelerometer, wherein the processor is configured to perform any of the steps of the method according to any of claims 1 to 11.

14. A non-transient memory storing program code instructions for use in a system for quantifying or determining an indication of cardiorespiratory fitness, wherein the system comprises (A) an accelerometer configured to be placed on the chest of a person for measuring accelerations and vibrations of the chest wall of the person caused by myocardial movement, and (B) a processor operatively connected to the accelerometer, wherein the program code instructions are configured, when executed by the processor, to perform the method according to any of claims 1 to 11.

\* \* \* \* \*